United States Patent
Want et al.

(10) Patent No.: US 6,358,218 B1
(45) Date of Patent: Mar. 19, 2002

(54) FLUID-RECOVERY SYSTEM WITH INTEGRALLY MOLDED COMPONENTS

(75) Inventors: Nicholas Want, Manchester; Theodore Karwoski, Hollis; Steve A. Herweck, Nashua; Thomas S. Cochran, Antrim; Scott E. Corbeil, Litchfield; David R. Autote; Ralph L. Gillis, both of Nashua, all of NH (US)

(73) Assignee: Atrium Medical Corporation, Hudson, NH (US)

( * ) Notice: Subject to any disclaimer, the term of this patent is extended or adjusted under 35 U.S.C. 154(b) by 0 days.

(21) Appl. No.: 09/358,944

(22) Filed: Jul. 22, 1999

Related U.S. Application Data
(60) Provisional application No. 60/118,034, filed on Jan. 29, 1999.

(51) Int. Cl.[7] ................................................. A61B 5/00
(52) U.S. Cl. ....................................... 600/573; 604/317
(58) Field of Search ......................... 600/579; 604/317, 604/318, 319, 320, 321, 323, 324

(56) References Cited

U.S. PATENT DOCUMENTS

| | | | |
|---|---|---|---|
| 3,363,626 A | 1/1968 | Eidwell et al. | |
| 4,084,606 A | * 4/1978 | Mittleman | 137/102 |
| 4,258,824 A | 3/1981 | Kurtz et al. | 181/233 |
| 4,544,370 A | 10/1985 | Elliott et al. | 604/319 |
| 4,550,749 A | 11/1985 | Krikorian | 137/843 |
| 4,605,400 A | 8/1986 | Kurtz et al. | 604/319 |
| 4,715,856 A | 12/1987 | Elliott et al. | 604/321 |
| 4,738,671 A | 4/1988 | Elliott et al. | 604/319 |
| 4,747,843 A | * 5/1988 | Felix et al. | 604/318 |
| 4,747,844 A | 5/1988 | Elliott | 604/319 |
| 4,988,342 A | 1/1991 | Herweck et al. | 604/321 |
| 5,114,416 A | 5/1992 | Karwoski et al. | 604/321 |
| D328,790 S | 8/1992 | Herweck et al. | D24/169 |
| 5,141,504 A | 8/1992 | Herweck et al. | 604/317 |
| 5,154,712 A | 10/1992 | Herweck et al. | 604/321 |
| D340,285 S | 10/1993 | Herweck et al. | D24/169 |
| 5,286,262 A | 2/1994 | Herweck et al. | 604/321 |
| 5,300,050 A | 4/1994 | Everett et al. | 604/320 |
| 5,380,314 A | 1/1995 | Herweck et al. | 604/403 |
| 5,397,299 A | 3/1995 | Karwiski et al. | 604/4 |
| 5,401,262 A | 3/1995 | Karwoski et al. | 604/321 |
| RE35,225 E | 4/1996 | Herweck et al. | 604/321 |
| 5,507,734 A | 4/1996 | Everett, Jr. et al. | 604/320 |
| 5,722,964 A | 3/1998 | Herweck et al. | 604/317 |
| 5,807,358 A | 9/1998 | Herweck et al. | 604/320 |
| 5,865,408 A | 2/1999 | Swisher et al. | 248/188.12 |

FOREIGN PATENT DOCUMENTS

WO    WO 98/30256    7/1998

* cited by examiner

Primary Examiner—Robert L. Nasser
Assistant Examiner—Pamela Wingood
(74) Attorney, Agent, or Firm—Lahive & Cockfield, LLP

(57) ABSTRACT

The present invention relates to fluid recovery systems for collecting fluid from a patient. A fluid recovery system according to the teachings of the invention includes a housing having a collection chamber for collecting fluid from a patient, and further includes a plurality of components and/or structures that are integrally formed with the housing. Such integrally molded components can include valves for controlling fluid flow within the fluid recovery system and a tamper resistant disposal system.

25 Claims, 14 Drawing Sheets

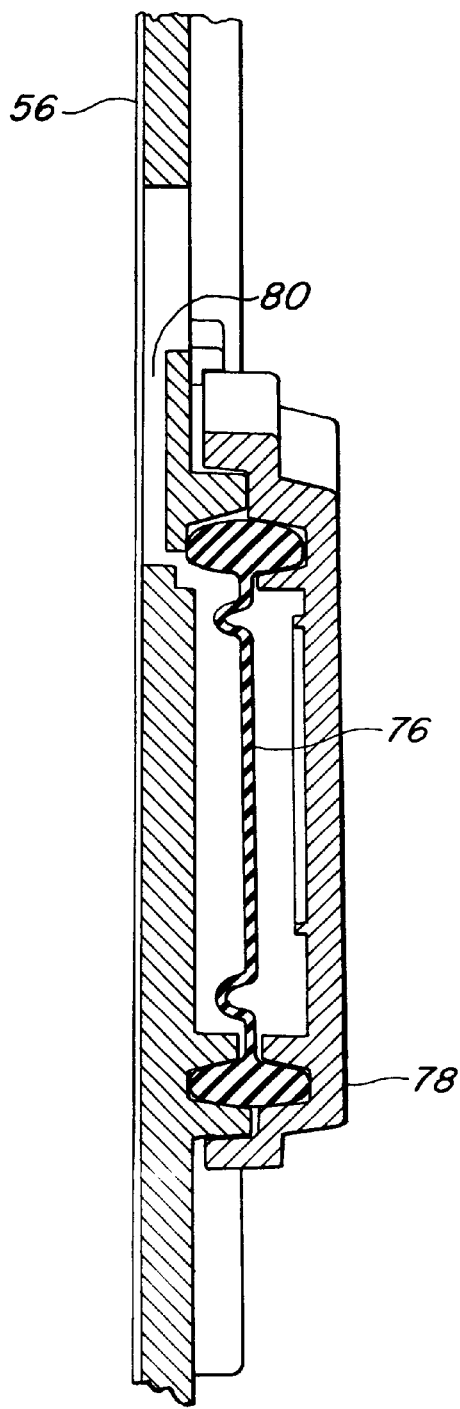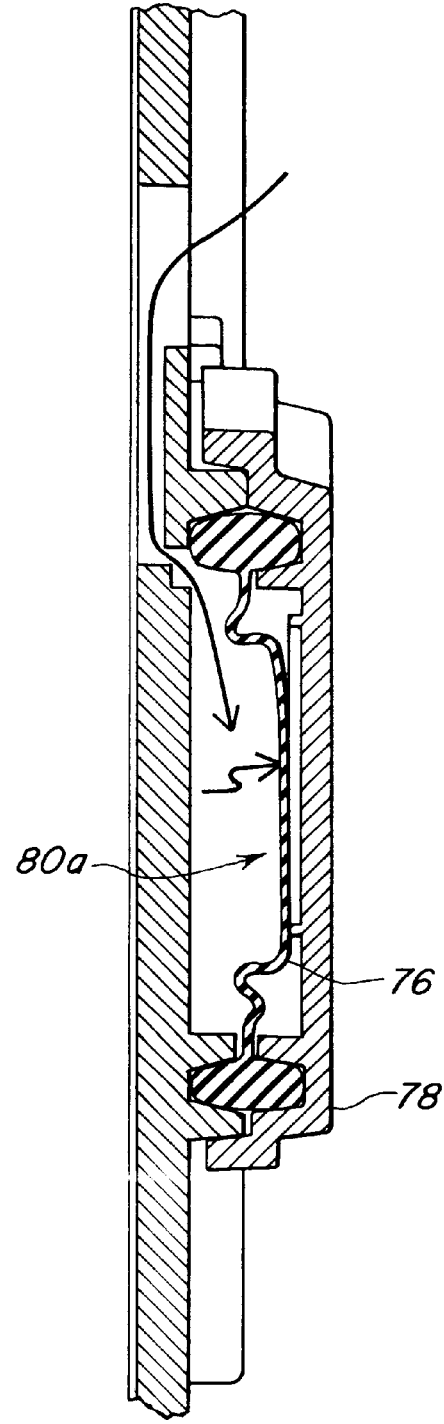
*FIG. 12A*      *FIG. 12B*

FLUID-RECOVERY SYSTEM WITH INTEGRALLY MOLDED COMPONENTS

RELATED APPLICATIONS

The present application claims priority to a provisional application entitled "Fluid Recovery System", filed on Jan. 29, 1999, and having a Ser. No. 60/118-034. This provisional application is herein incorporated by reference.

BACKGROUND OF THE INVENTION

The present invention relates to apparatuses for draining fluid from a patient, and more particularly, to fluid recovery systems for draining blood from the thoracic cavity of the patient.

A number of fluid-recovery systems have been developed for drawing fluid, such as blood, from a patient. Such devices generally apply suction to a body cavity of the patient to remove blood or other fluid after trauma or surgery. For example, a chest drain is a relatively compact bedside fluid-recovery system that is employed to collect fluids post-operatively from a closed surgical site through a drain tube implanted in the patient's chest.

Conventional fluid-recovery systems typically include a housing and a number of components, such as valves and ports, that are manufactured separately from the housing, and subsequently attached to the housing. Such separate manufacturing of the components increases the number of steps in the manufacturing process, thereby increasing the manufacturing cost. Further, additional costs are incurred for assembling these components to the housing. Moreover, each separately manufactured component may need to be individually calibrated, further increasing the manufacturing cost of the system.

Accordingly, there is a need for a fluid-recovery system that requires fewer number of steps for its manufacturing, and further minimizes the need for calibration of its components.

SUMMARY OF THE INVENTION

The present invention provides a fluid-recovery system for collecting fluid from a patient which includes a housing having various integrally molded components and/or structures. The term integrally molded, as used herein, refers to forming a particular component and/or structure of the housing of the fluid-recovery system as a single unit with the remaining parts of the housing. In other words, an integrally molded component and/or structure is not added to a pre-formed housing, but rather is formed with other parts of the housing as a single unit. In particular, the integrally molded components and/or structures of the housing are not intended to be removed and/or replaced.

In one aspect, the present invention provides a fluid-recovery system having a housing and a valve for controlling fluid flow within the fluid-recovery system. The housing includes a collection chamber for collecting the fluid, and the valve includes a valve member that selectively engages a valve seat surrounding a fluid opening, to seal the opening. The valve seat is integrally molded to the housing of the fluid recovery system.

According to one aspect of the invention, the valve for controlling fluid flow within the fluid-recovery system is a vacuum protection valve that provides air flow communication with the collection chamber to permit air flow in one direction out of the collection chamber. In one preferred embodiment of the invention, the valve member of the vacuum protection valve is constructed of an elastomeric material and has a generally umbrella-like shape.

In another aspect, the present invention provides a fluid recovery system for collecting fluid from a patient that includes a housing having a collection chamber for collecting a volume of the fluid from the patient, and a vacuum protection valve for allowing air flow in one direction out of the collection chamber. The vacuum protection valve further includes an enclosure that is integrally molded within the housing.

In a preferred embodiment of the invention, the vacuum protection valve includes a flexible retaining member whose snap-action placement within the integrally molded enclosure secures the valve to the housing. The integrally molded enclosure can have a base extending to an opening that is sized and shaped to engage the flexible retaining member of the valve, thereby attaching the valve to the housing. The vacuum protection valve can include a valve body having an opening therein, and an umbrella valve member that is seated within the valve body to seal the opening. The umbrella valve member provides one way air flow through the opening when the pressure in the collection chamber exceeds a pre-defined threshold.

According to another aspect of the invention, the valve for controlling fluid flow within the fluid-recovery system is a negative pressure protection valve that opens to provide air flow between the collection chamber and the outside environment through the fluid opening when pressure in the collection chamber is lower than a predefined threshold.

In a preferred embodiment of the invention, the negative pressure protection valve can include a valve housing for seating a spring, and the valve member. The spring biases the valve member against the integrally molded valve seat to seal the fluid opening. A pressure in the collection chamber that is lower than the predefined threshold causes the spring to contract, thereby moving the valve member and providing air flow between the collection chamber and the outside environment. The negative pressure protection valve can optionally include a filter to filter the air before it enters the collection chamber. The valve housing can be integrally molded to the housing of the fluid recovery system. Alternatively, the valve housing can be a separate component that is seated within the integrally molded enclosure. The valve housing can include a first cylindrically tubular portion for receiving the spring and extending to a second portion for seating the valve member. The second portion of the valve housing can have at least one port therein for providing air flow between the valve housing and the collection chamber.

Accordingly to one aspect of the invention, an integrally molded raised structure protruding outwardly from the fluid opening of the negative pressure protection valve inhibits occlusion of the opening. The raised structure can include a hollow frusto-conical member that surrounds the fluid opening from the outside and has ports therein for providing air flow from the outside environment through the fluid opening.

According to yet another aspect of the present invention, a fluid-recovery system is provided that includes a collection chamber for collecting a volume of fluid from a patient, and a positive pressure relief valve for reducing pressure in the collection chamber when pressure in the chamber exceeds a pre-defined value. The pressure relief valve includes an integrally molded enclosure formed in the housing, and further includes an integrally molded ramped rib. The integrally molded enclosure of the pressure relief valve can include a first opening for providing air flow communication with the collection chamber, and a second opening for providing air flow communication with the outside environment. The first opening can have a tapered portion for seating a sealing ball that seals the first opening to provide a fluid-tight seal between the collection chamber and the integrally molded enclosure.

When pressure within the collection chamber exceeds a pre-defined value, it dislodges the ball from the first opening to allow air flow between the collection chamber and the outside environment. The integrally molded ramped rib provides a rolling surface for the sealing ball to bias the ball toward the first opening when the fluid recovery system is destabilized from a normal operating orientation. The term "destabilized" as used herein refers to situations or conditions in which the fluid recovery device is bumped, jarred, pushed, tipped or completely knocked-over, resulting in the device being positioned, temporarily or permanently, in an orientation other than its normal, preferred operating orientation, i.e., an orientation in which the fluid recovery system is upright. The pressure relief valve can include a raised surface surrounding the second opening to provide a seat for a sealing element that can seal the housing from the outside environment, for example when pressure testing the fluid-recovery system.

In another aspect, the fluid-recovery system of the invention can include a housing having a front face, a collection chamber integrally formed within the housing for collecting fluid, and a vacuum indicator for indicating when pressure in the collection chamber is below a selected threshold. The vacuum indicator includes a seat integrally molded in the front face of the housing, a translucent diaphragm, preferably formed of an elastomeric material, positioned in the seat, and a cap that is mounted to the seat to compress the diaphragm into sealing engagement with the seat. The cap has an opening therein that provides air flow between the collection chamber and the diaphragm, and further has a marking on a surface facing the diaphragm. When the pressure in the collection chamber is below the selected threshold, a pressure differential across the diaphragm develops that forces the diaphragm to contact the inside surface of the cap, thereby rendering the marking inside the cap discernable.

Alternatively, the front face can include a translucent portion, and the vacuum indicator can be a separate component that is positioned within the housing such that it is externally visible through the translucent portion of the front face.

In yet another aspect, the present invention provides a fluid-recovery system having a top surface, a collection chamber for collecting a volume of fluid from a patient, and a manually actuable pressure relief valve. The manually actuable relief valve includes an integrally molded enclosure within the top surface that is in air flow communication with the collection chamber. The integrally molded enclosure is sealed from the outside environment by a manually actuable diaphragm that is actuated by an integrally molded actuating element to provide air flow between the collection chamber and the outside environment to reduce pressure in the collection chamber.

Another aspect of the invention relates to providing a fluid-recovery system having a top surface, a collection chamber for collecting fluid from a patient, and a connecting element of a latching connector that is integrally molded to the top surface of the housing, and is configured to receive a mating connecting element of the latching connector. In one preferred embodiment of the invention, the connecting element is a female portion of a latching connector. In another preferred embodiment of the invention, the connecting element is a male portion of a latching connector.

In yet another aspect, the invention provides a fluid-recovery system having a housing that includes a collection chamber, and a pressure measuring port integrally molded within the housing. The integrally molded pressure port is configured to be in fluid communication with the collection chamber, and to receive a pressure gauge for measuring pressure within the collection chamber.

Another aspect of the fluid recovery system of the invention relates to a tamper-resistant disposal system for disposal of fluid collected within the collection chamber. The tamper-resistant system can preferably include a disposal port integrally molded to the housing, a seal positioned on the disposal port for sealing the disposal port, and a cap positioned over the seal and secured to the disposal port, to provide a air-tight seal of the disposal port. In a preferred embodiment of the invention, the cap includes a cap body, a cap base, and a plurality of break-away tabs along a circumference thereof, joining the cap body to the cap base. The cap further includes a plurality of ratchet-like teeth that can matingly engage with a plurality of ratchet-like teeth on the disposal port upon threaded engagement of the cap with the disposal port. The mating engagement of the two sets of teeth inhibits rotation of the base of the cap relative to the disposal port when the cap body is rotated relative to the disposal port. The cap can include a translucent portion to allow visual inspection of the seal.

Another aspect of the invention relates to providing a handle for the fluid-recovery system of the invention that is sized and shaped such that it allows safe and easy transport of the fluid-recovery system from one location to another. Such a handle is preferably formed as an integral part of the housing of the fluid recovery system, and is raised above other components on the top surface of the fluid recovery system. The length of the handle is selected such that it allows two people to simultaneously hold it. For example, in a preferred embodiment of the invention, the handle is approximately 5 inches long. Nevertheless, those skilled in the art will appreciate that handles having other lengths may be used to practice the present invention.

A preferred method for manufacturing various embodiments of the present invention includes forming a housing through an injection molding process, wherein the housing includes a collection chamber for collecting fluid and further includes other integrally molded components and/or structures for providing a number of different functions, such as relieving excess pressure in the collection chamber or indicating that the pressure in the collection chamber is below a selected threshold. For example, the injection molding process can be utilized to form an integrally molded enclosure within the housing for matingly engaging a vacuum protection valve.

These and other features and advantages of the present invention will be more fully understood by reference to the following detailed description in conjunction with the attached drawings in which like reference numerals refer to like elements through the different views.

BRIEF DESCRIPTION OF THE DRAWINGS

FIG. 12A is a side-elevational view in cross-section of the assembled vacuum indicator of FIGS. 11A and 11B when the collection chamber is not under vacuum and hence the diaphragm of the vacuum indicator is in a relaxed position.

FIG. 12B is a side-elevational view in cross-section of the vacuum indicator of FIG. 12A when the collection chamber is under vacuum and the diaphragm of the vacuum indicator is forced against the inner surface of the cap, thereby rendering the marking on the inner surface of the cap visible.

DETAILED DESCRIPTION OF THE INVENTION

A fluid-recovery system in accordance with the teachings of the invention includes a housing having a collection chamber for collecting fluid from a patient, and further includes a plurality of integrally molded components and/or structures within the housing, such as integrally molded enclosures for housing valves for controlling fluid flow within the fluid recovery system. The provision of integrally molding components within the housing of the system simplifies manufacturing of the system by reducing the number of necessary components and the number of manufacturing steps, thus resulting in significant reduction in manufacturing costs.

Figure 1:
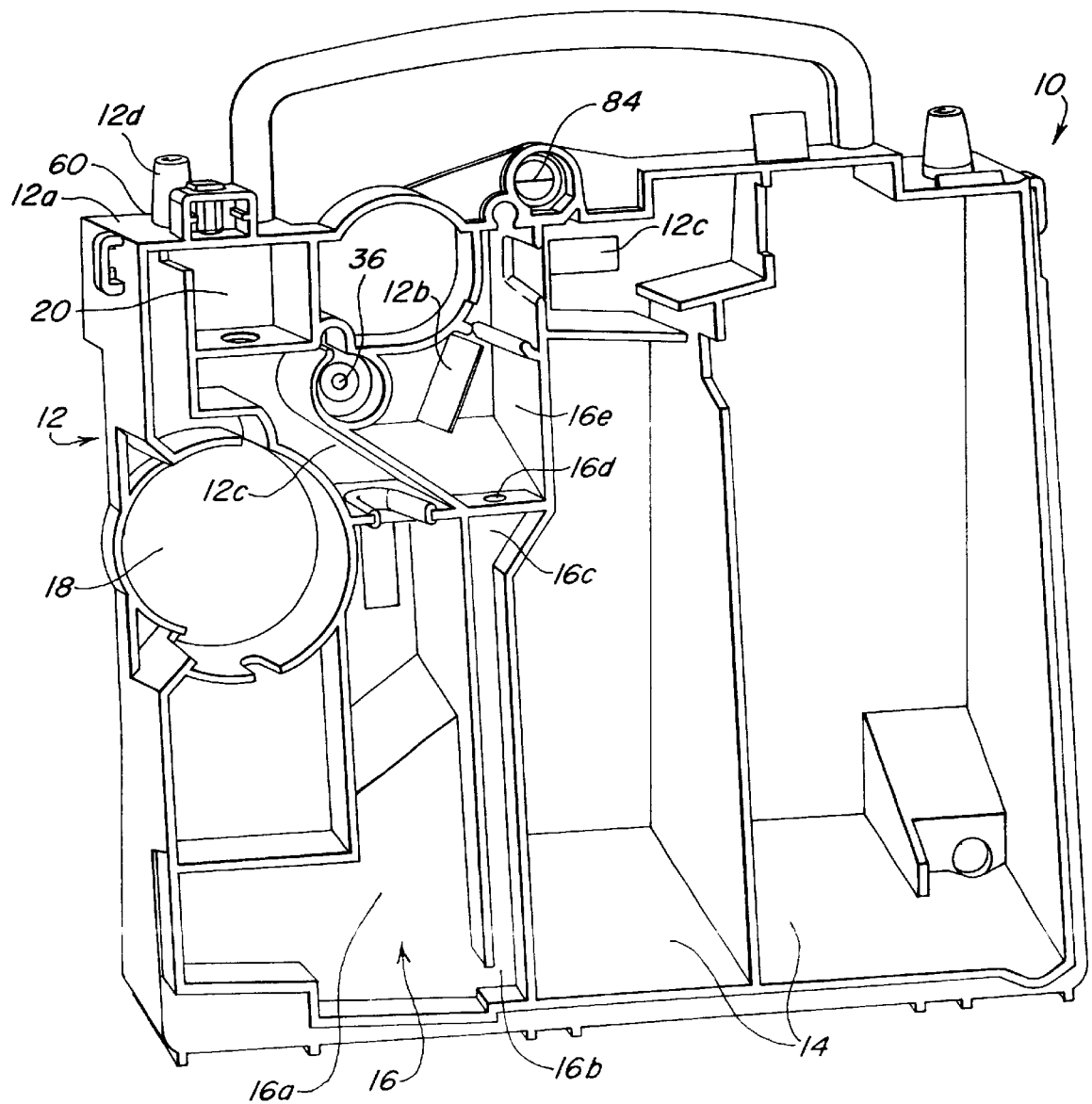
FIG. 1 is a perspective view of a fluid recovery system according to the present invention with the front cover removed having various integrally molded components and structures.
Figure 2:
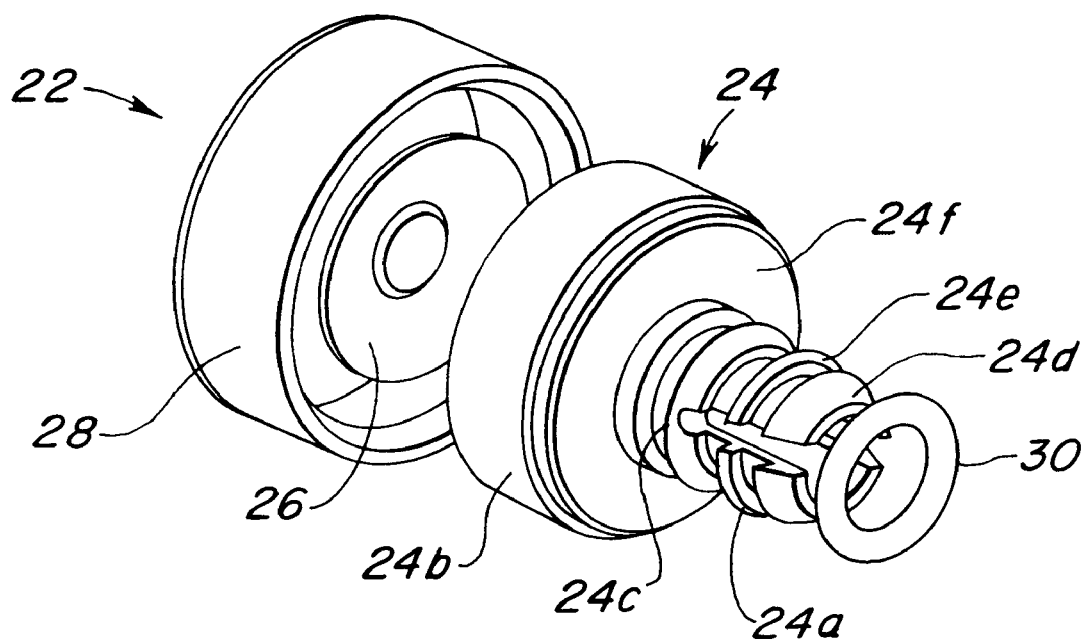
FIG. 2 is an exploded perspective view of a vacuum protection valve that is engageably received within an integrally molded enclosure of the fluid-recovery system of FIG. 1, to relieve pressure in the collection chamber.

An illustrative fluid-recovery system 10 according to the present invention, shown in FIG. 1, includes a housing 12 having a collection chamber 14 for collecting fluid from a patient, an air leak monitor chamber 16, and a valve housing 18 for a suction-regulating valve (not shown). The housing 12 further includes a plurality of integrally molded components therein, as described in more detail below.

The air leak monitor chamber 16 includes a large column 16a, and a narrow column 16b that extends to a portion 16c having an opening 16d. The opening 16d can include a circular portion and notched portion extending radially from the circular portion. The air leak monitor chamber 16 is in air flow communication with the collection chamber 14 through the opening 16d, and anti-spill nozzles 12b and 12c. The structure and operation of the anti-spill nozzles 12b and 12c are provided in a concurrently filed application entitled "Fluid Recovery Device and Flow Member for Inhibiting Undesired Fluid Flow", Ser. No. 09/359,533, herein incorporated by reference. The air leak monitor chamber 16 is typically filled with a few centimeters of water. In the event of an air leak from the patient into the collection chamber 14, the air travels from the collection chamber 14 to the air leak monitor chamber 16, bubbling through the water in the air leak monitor chamber as it passes through the chamber 16. This bubbling of the air through the water in the chamber 16 alerts a medical professional to the presence of the air leak. Further, a float ball (not shown) rides up and down the narrow column 16b. In the event of a high negative pressure, the float ball partially occludes the opening 16d, for example by occluding the circular portion of the opening 16d, to impede the flow of water through the opening 16d. The water leaking through the opening 16d collects harmlessly above the float ball and ultimately returns to the column 16b when suction reaches normal levels.

The structure of and operation of the air leak monitor chamber including the float ball are described in detail in U.S. Pat. No. 5,807,358 (herein "'358 patent"), and U.S. Pat. No. 5,114,416 (herein "'416 patent"), both of which are herein incorporated by reference.

The suction regulating valve sets the amount of suction applied through a port 12d at a user-set level in a range of −10 to −40 centimeters of water by controlling the amount of air entering the housing 12. The structure and operation of the suction regulating valve are described in detail in the aforementioned '358 patent.

With reference to FIGS. 1, 2, 3A, 3B, 3C, 4, and 5, the housing 12 includes an integrally molded enclosure 20 for matingly engaging a vacuum protection valve 22. The enclosure 20 is formed in the housing 12, preferably during an injection molding process such that the enclosure 20 forms an integral component of the housing 12. The illustrative vacuum protection valve 22 includes a valve body 24, a valve member 26 that is constructed of an elastomeric material and has a generally umbrella-like shape, a retaining member 28, and an O-ring 30. The retaining member 28 retains the umbrella valve member 26 within the enclosure 20, and the umbrella valve member 26 seals an opening within the enclosure 20, as described below. The valve body 24 includes one or more resilient legs 24a extending from a cylindrical housing 24b. The legs 24a are preferably constructed from a resilient material, for example a plastic or an elastomeric material, that permits the legs to flex from a compressed position to a relaxed position. The valve body 24 includes a groove 24c for seating the O-ring 30 therein, and further includes an angled retaining member 24d. Each resilient leg further includes a rib 24e between the O-ring groove 24c and the retaining member 24d.

Figure 3C:
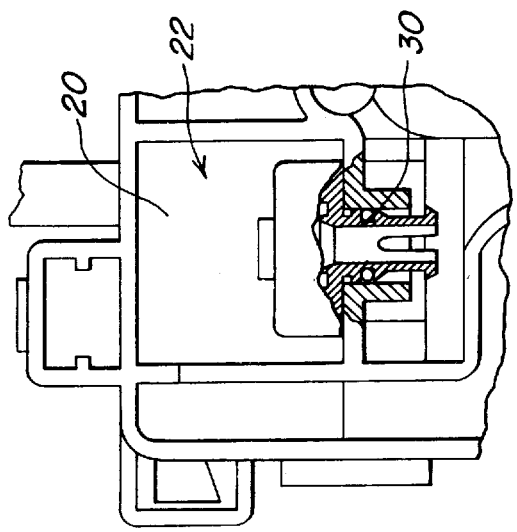
FIG. 3C is a fragmentary front-elevational view in cross-section of the fluid recovery system of FIG. 1, illustrating a mating engagement of the vacuum protection valve of FIG. 3B within the tapered opening of the integrally molded enclosure for receiving the vacuum valve, and further illustrating an O-ring sealing against the interior surface of the tapered opening.
Figure 3B:
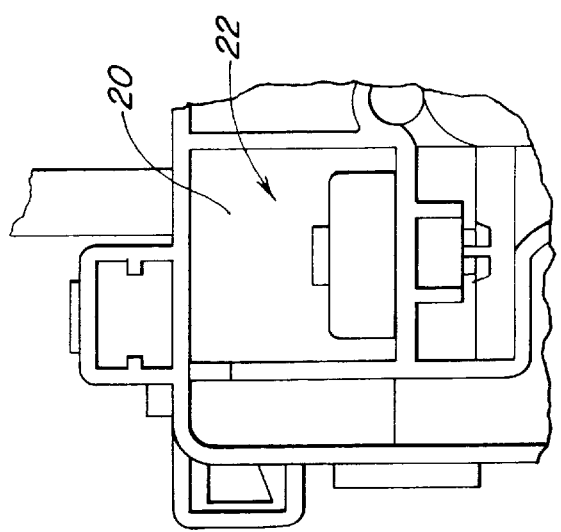
FIG. 3B is a fragmentary front-elevational view in cross-section of the fluid-recovery system of FIG. 1, illustrating the vacuum protection valve of FIG. 3A matingly engaged within the integrally molded enclosure for receiving the vacuum protection valve.
Figure 3A:
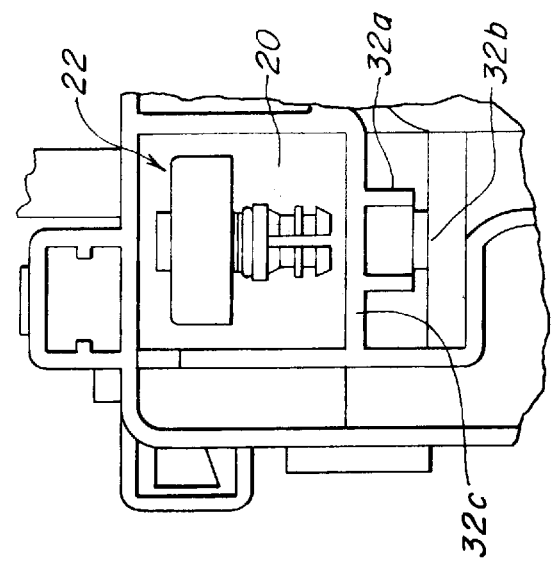
FIG. 3A is a fragmentary front elevational view in cross-section of the fluid-recovery system of FIG. 1, illustrating an integrally molded enclosure for receiving the vacuum protection valve of FIG. 2, and further illustrating the vacuum protection valve before mating engagement within a tapered opening of the integrally molded enclosure.

With reference to FIG. 3A, the integrally molded enclosure 20 includes a base 33 extending to a tapered section 32a having an opening 32b therein for receiving the resilient legs 24a. A snap-action placement of the resilient legs 24a within the opening 32b matingly engages the valve body 22 within the enclosure 20, as shown in FIG. 3B, with the angled retaining member 24d protruding through the opening 32b to prevent the vacuum protection valve 22 from dislodging from the enclosure 20. Further, FIG. 3C shows that upon engagement of the valve 22 within the enclosure 20, the O-ring 30 contacts the inner surface of the tapered portion 32a.

Figure 4:
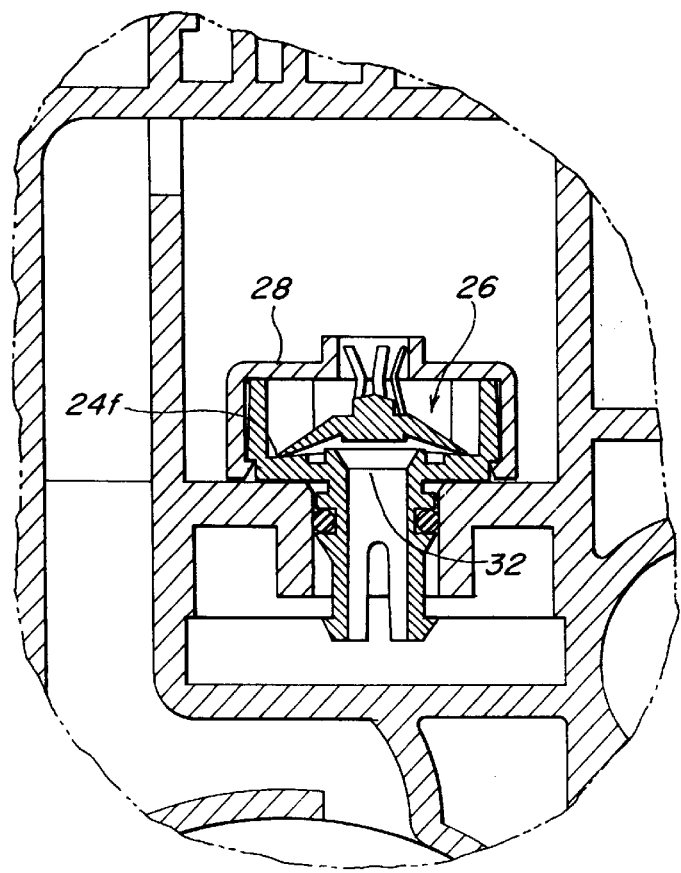
FIG. 4 is a fragmentary front-elevational view in cross-section of the fluid-recovery system of FIG. 1, illustrating the vacuum protection valve of FIG. 3 seated in its integrally molded enclosure in a closed position, wherein an umbrella valve member of the valve seals the tapered opening of the integrally molded enclosure.

The vacuum protection valve 22 operates as a one-way valve, also known as a check valve, prohibiting air flow in one direction and allowing air flow in the opposite direction. Specifically, the retaining member 28 holds the umbrella valve member 26 in place against a valve seat 24f to seal the opening 32b when there is no air flow through the valve, as shown in FIG. 4.

Figure 5:
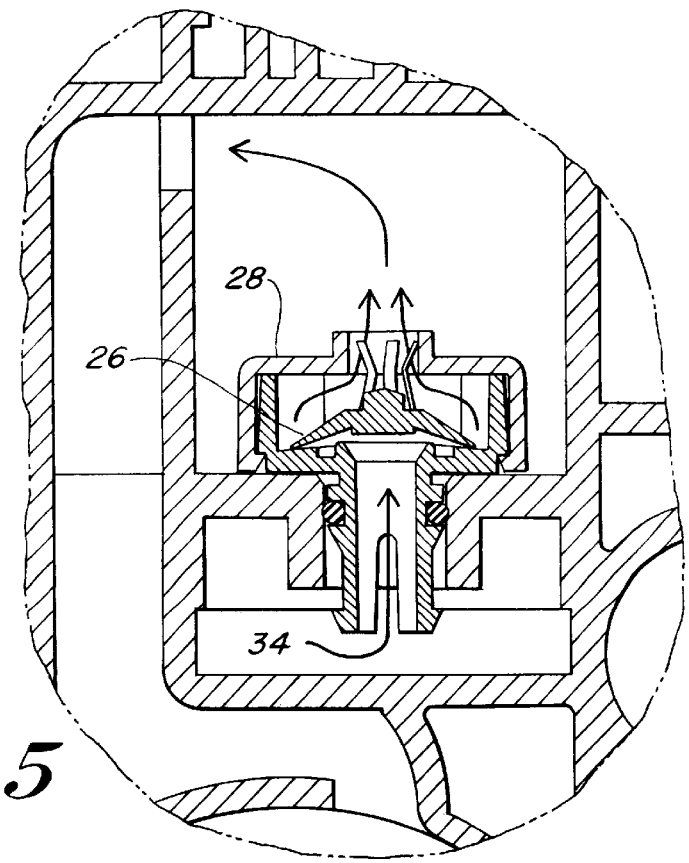
FIG. 5 is a front-elevational view in cross section of the fluid recovery system of FIG. 3, illustrating air flow through the vacuum protection valve of FIG. 3 when the valve is an open position.

In normal operation, i.e., when the fluid-recovery system is connected to a patient and suction is applied, the vacuum protection valve 22 is open, thus allowing air flow from the air leak monitor chamber 16 through an opening 16e (FIG. 1), via a channel 12e curved around the suction regulating valve, into a vacuum port 12d (FIG. 1) that is connected to a pump (not shown). FIG. 5 illustrates the flow of air through the vacuum protection valve 22 when the valve 22 is open. In particular, arrows 34 depict the movement of air through the vacuum protection valve 22. The air pressure exerted on the inner surface of the umbrella valve member 26 lifts the edge of the umbrella valve member 26 to allow the air to flow between the resilient legs 24a into the enclosure 20.

If the enclosure 20 is exposed to an atmospheric pressure while the collection chamber 14 is under vacuum, for example if the suction line connecting the port 12d to a pump is accidentally disconnected, the vacuum protection valve 22 closes, thus preserving the vacuum within the collection chamber 14. The closing of the valve 22 occurs because the pressure differential across the umbrella member 26 forces the edges of the umbrella member 26 against the valve seat 24f (FIG. 4).

Figure 5A:
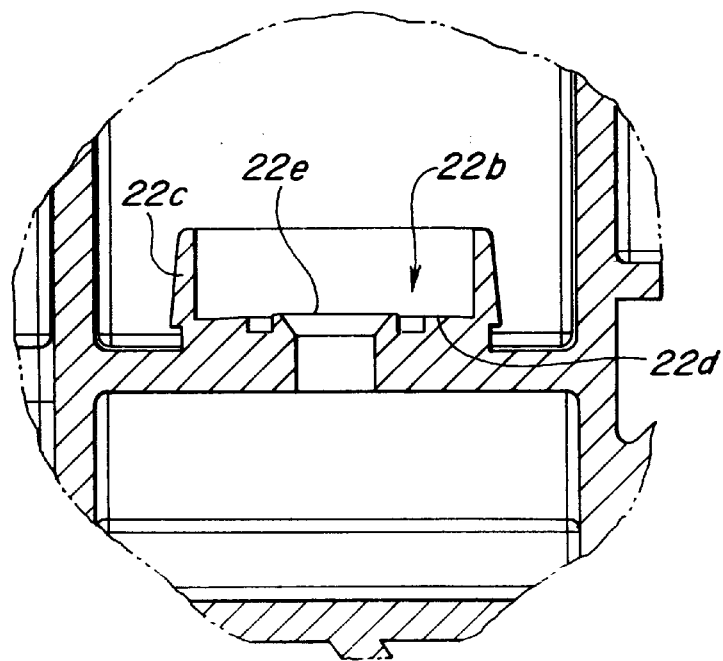
FIG. 5A is a fragmentary front-elevational view in cross-section of an integrally molded valve seat of a vacuum protection valve according to the teachings of the present invention.
Figure 5B:
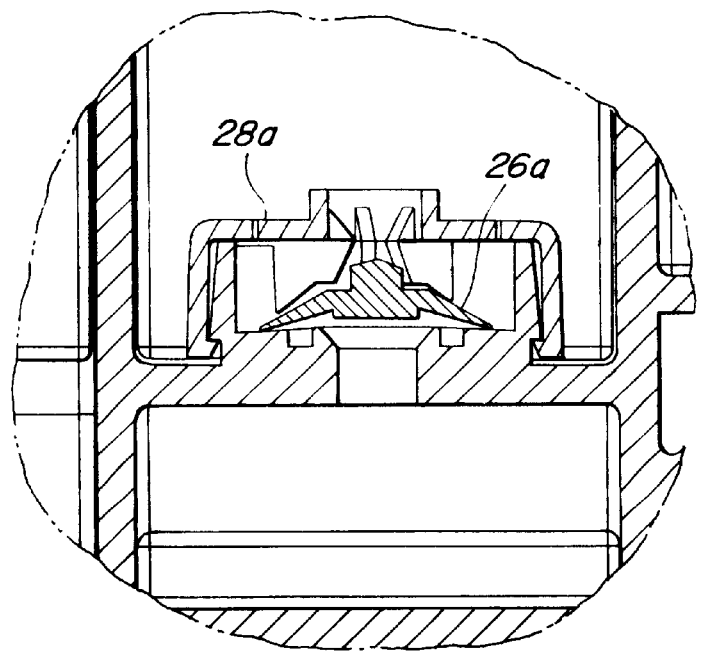
FIG. 5B is a fragmentary front-elevational view in cross-section of a retaining member and a valve member coupled to the integrally molded valve seat of FIG. 5A to form a vacuum protection valve according to the teachings of the present invention.

An alternative embodiment of a vacuum protection valve according to the teachings of the present invention, shown in fragmentary views of FIGS. 5A and 5B as a valve 22a, includes a valve seat 22b that is integrally molded to the housing 12. The illustrated integrally molded valve seat 22b includes a wall 22c surrounding a base 22d that extends to an opening 22e. A retaining member 28a (FIG. 5B) holds a valve member 26a, which is constructed of an elastomeric material and has a generally umbrella-like shape, in position over the opening 22e and against the base 22d of the integrally molded valve seat 22b, to seal the opening 22e. The vacuum protection valve 22a operates in the same manner as the vacuum protection valve 22, discussed above.

Figure 6B:
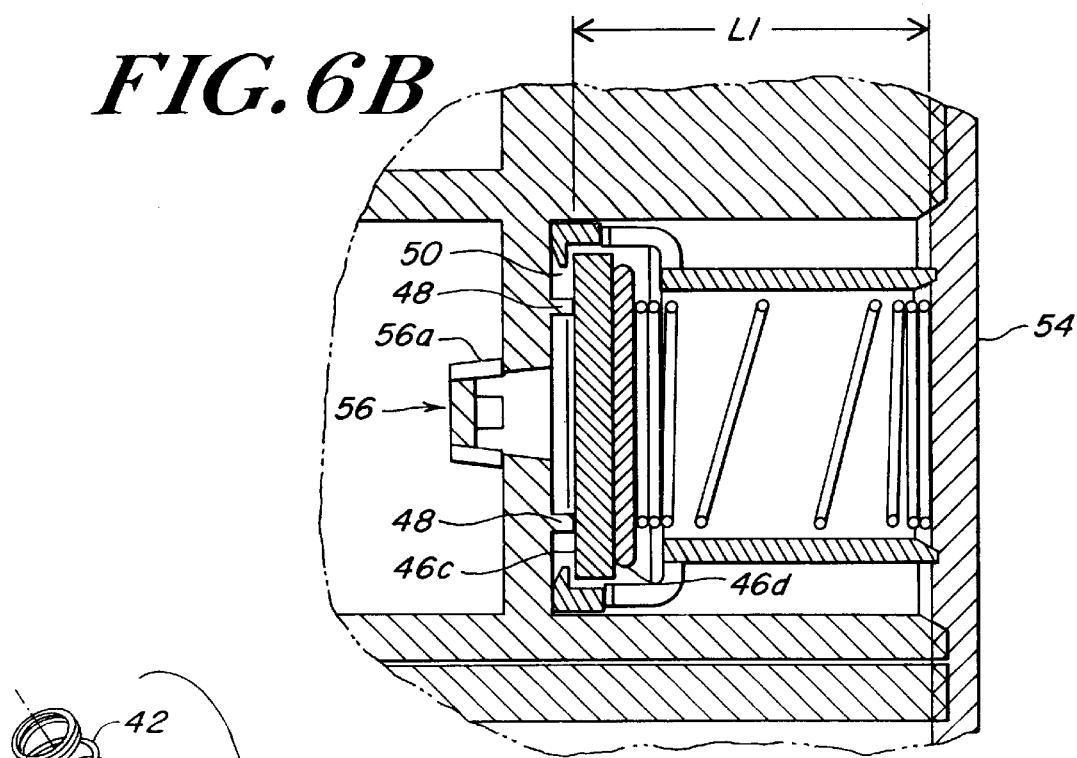
FIG. 6B is a side-elevational view in cross-section of the fluid recovery system of FIG. 6A, illustrating the negative pressure protection valve of FIG. 6A assembled and seated within the integrally molded enclosure for receiving the valve, and further illustrating a raised structure for inhibiting occlusion of the opening to the valve.
Figure 6A:
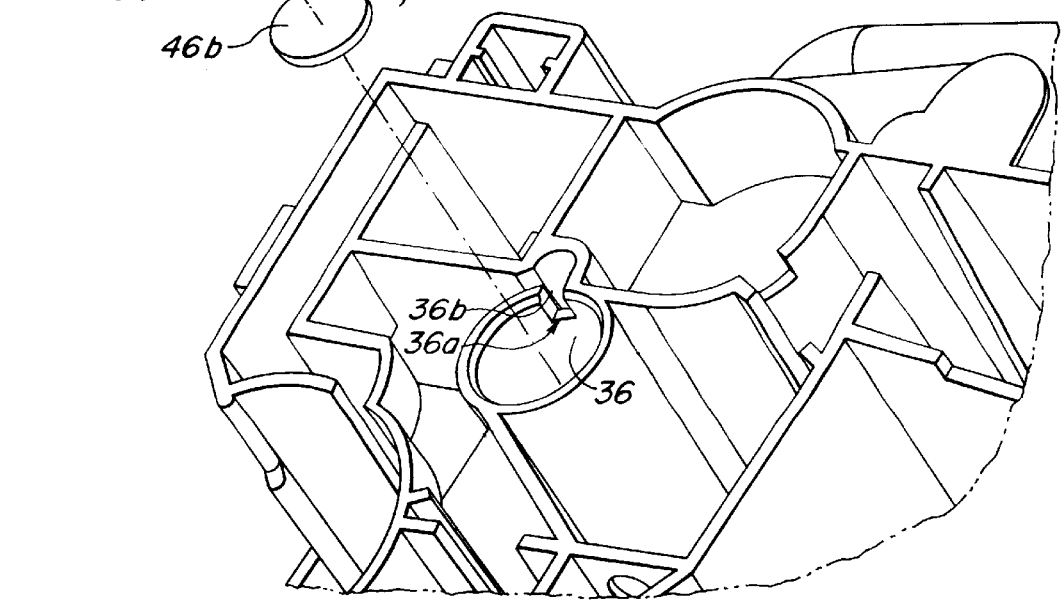
FIG. 6A is a fragmentary perspective view of the fluid-recovery system of FIG. 1, illustrating an integrally molded enclosure for receiving a negative pressure protection valve, and further illustrating various components of the negative pressure protection valve in an exploded view.

Referring to FIGS. 1, 6A, and 6B, the housing 12 further includes an integrally molded enclosure 36 that is in air flow communication with the collection chamber 14 through the anti-spill nozzles 12b and 12c. The enclosure 36 houses a negative pressure protection valve 38 that is configured to open when pressure in the collection chamber is lower than a pre-defined threshold, to provide air flow between the collection chamber and the outside environment. Such an air flow ensures that the pressure within the collection chamber remains within a safe range. The pre-defined threshold at which the negative pressure protection valve 38 opens is selected to be preferably in the range of −55 to −75 centimeters of water.

The illustrative negative pressure protection valve 38 includes a valve housing 40 for seating a spring 42, a valve member 44 in the form of a spring washer 46a, and a sealing element 46b. The spring washer 46a is preferably formed of stainless steel or the like, and the sealing element 46b is preferably formed of an elastomeric material. In an alternative embodiment, the valve member 44 is formed in one piece having one surface that is formed of a hard material, such as stainless steel, and an opposed surface that is formed of an elastomeric material. The valve housing 40 is preferably integrally molded within the enclosure 36. Alternatively, the valve housing 40 is a separate component that is seated within the enclosure 36.

Upon placement of the negative pressure valve 38 within the enclosure 36, the valve member 44 is seated over an integrally molded valve seat 48 protruding above a base 50 of the enclosure 36. In particular, the sealing element 46b covers an opening 52, that provides access to the outside environment, to seal the enclosure 36 from the outside environment when the negative protection valve 38 is closed. The spring washer 46a is seated over the sealing element 46b, to distribute the load from the spring 42 onto the sealing element 46b. The spring 42 fits within the valve housing 40 and is sized to provide the requisite amount of force on the spring washer 46a, and consequently on the sealing element 46b, such that the valve 38 opens at a desired pressure. A front cover 54 is positioned on the front face of the housing 12, and engages the valve housing 40 and the spring 42, to seal the valve 38 within the integrally molded enclosure 36.

Figure 7:
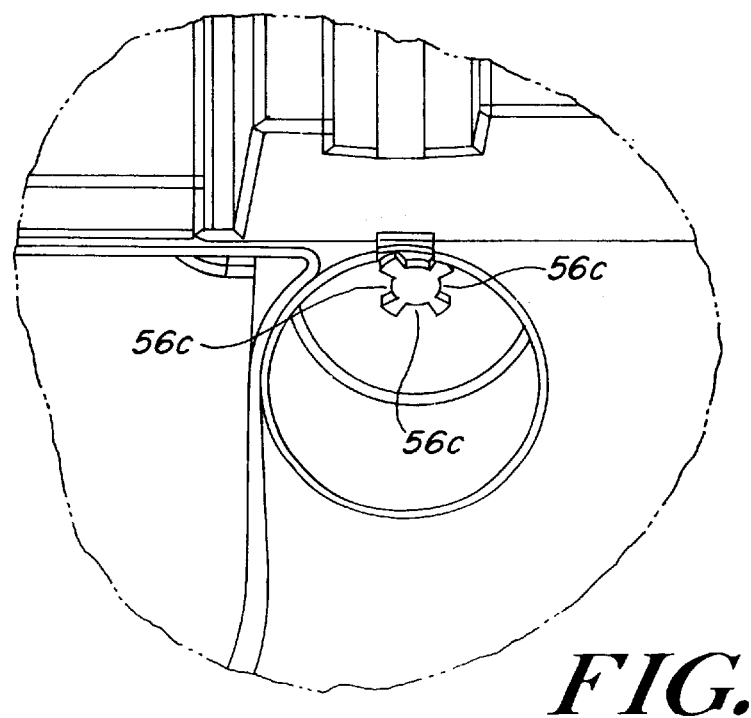
FIG. 7 is a fragmentary perspective view of the back surface of the fluid-recovery system of FIG. 1, illustrating the raised structure for inhibiting occlusion of the valve opening of FIG. 6B.

The illustrative integrally molded enclosure 36 includes an integrally molded raised structure 56 having a frusto-conical hollow member 56a that surrounds the opening 52 on the back surface of the housing 12. FIG. 7, which is a fragmentary view of the back surface of the housing 12, illustrates that the hollow member 56a includes a plurality of ports 56c therein that allow air flow from the outside environment through the opening 52. The raised structure 56 inhibits occlusion of the opening 52 by external objects. For example, if a medical professional inadvertently places a finger on the hollow member 56a, the openings 56c remain unoccluded, thereby ensuring that pressure on a surface 46c of the sealing element 46b remains at an atmospheric level (FIG. 6B).

Further, the illustrative valve housing 40 includes ports 40a that provide air flow communication between the inner portion of the valve housing 40, i.e., the portion within which the spring 42 is seated, and the remaining volume of the enclosure 36. Thus, the inner portion of the valve housing 40 is in air flow communication with the collection chamber 14. The surface 46c of the sealing element 46b is exposed to atmospheric pressure, and a surface 46d of the sealing element 46b is exposed to the pressure within the collection chamber 14. Thus, there exists a pressure differential across the sealing element 46b. When the valve 38 is closed, i.e., when pressure in the collection chamber 14 is above the pre-defined threshold, the pressure differential across the sealing element 46b is fully counter-acted by the compression force of the spring 42. That is, the spring 42 presses the spring washer 46a, and the sealing element 46b against the valve seats 48 with sufficient force to seal the opening 52. However, as the pressure within the collection chamber 14 begins to fall below the pre-defined threshold, the pressure differential across the sealing element 46b dislodges it from the valve seat 48 and compresses the spring 42 toward the front cover 54, thus opening the valve 38.

Figure 8:
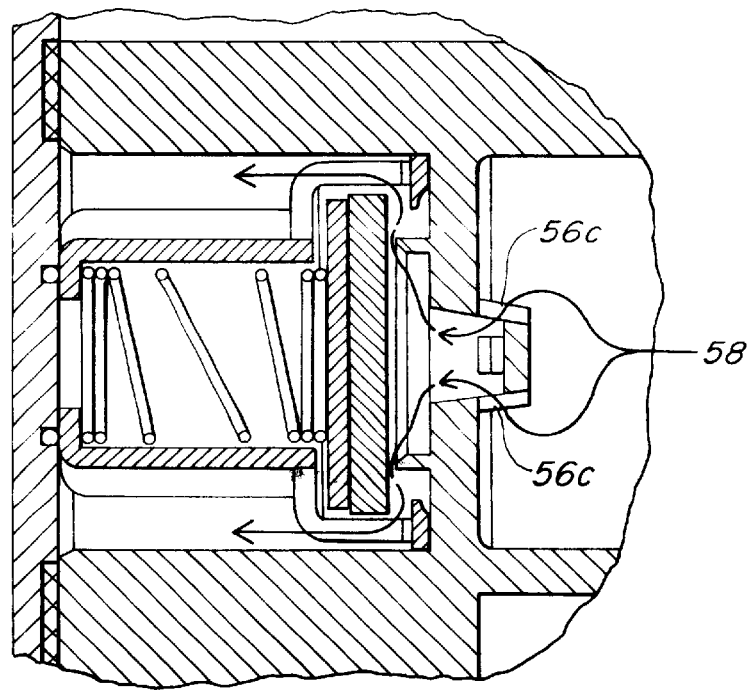
FIG. 8 is a fragmentary, side elevational view in cross-section of the fluid recovery system of FIG. 1, illustrating schematically air flow through the negative pressure protection valve of FIG. 6b when the valve is in an open position.

FIG. 8 illustrates the flow of air through the valve 38 when it opens. In particular, arrows 58, depicting the air flow through the valve 38, indicate that air enters the opening 52 from the outside environment through the ports 56c in the raised structure 56. This air flow exerts a pressure on the surface 46a of the sealing element 46. When the pressure in the collection chamber, and consequently the pressure on surface 46d of the sealing element 46b, is lower than the pre-defined threshold, the differential pressure across the sealing element 46b is sufficient to dislodge it from the valve seats 48. This allows air to flow from the outside environment through the ports 56c into the inner portion of the valve housing 40, and through the ports 40a into the remaining volume of the enclosure 36, and through a notched opening 36a (FIG. 6A) to the collection chamber 14. A filter can be optionally placed in a hollow cylindrical portion 36b of the notched opening 36a to filter the air before it enters the collection chamber 14. The air flow from the outside environment into the enclosure 36 lowers the pressure differential across the valve member 44 until the pressure differential across the valve member 44 is at a level at which the force of the spring 42 against the valve member 44 is sufficient to seat the sealing element 46b on the valve seat 48, thereby sealing the enclosure 36 from the outside environment.

One advantage of the illustrated integrally molded enclosure 36 is that a distance L1 (see FIG. 6B) between the valve seat 38 and the front face of the housing 12 is fixed for each housing manufactured. This distance and the pressure at which the valve 38 is desired to open are the design parameters that determine the spring constant of the spring 42. Thus, for a given set of design parameters, no separate calibration of the spring 42 for different fluid-recovery systems is required. That is, once a spring with a particular spring constant is shown to work properly in a fluid-recovery system according to the present invention, other springs having the same spring constant can be utilized in other similar fluid-recovery systems without a need for a separate calibration.

Figure 9A:
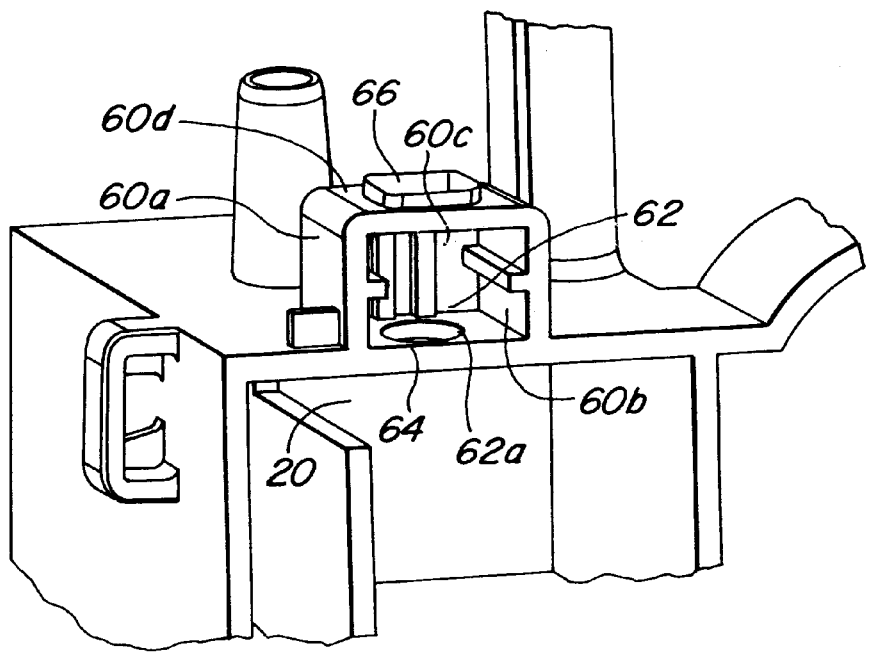
FIG. 9A is a fragmentary perspective view of the top surface of the fluid-recovery system of FIG. 1, illustrating a positive pressure relief valve integrally molded within the housing of the fluid-recovery system.
Figure 9B:
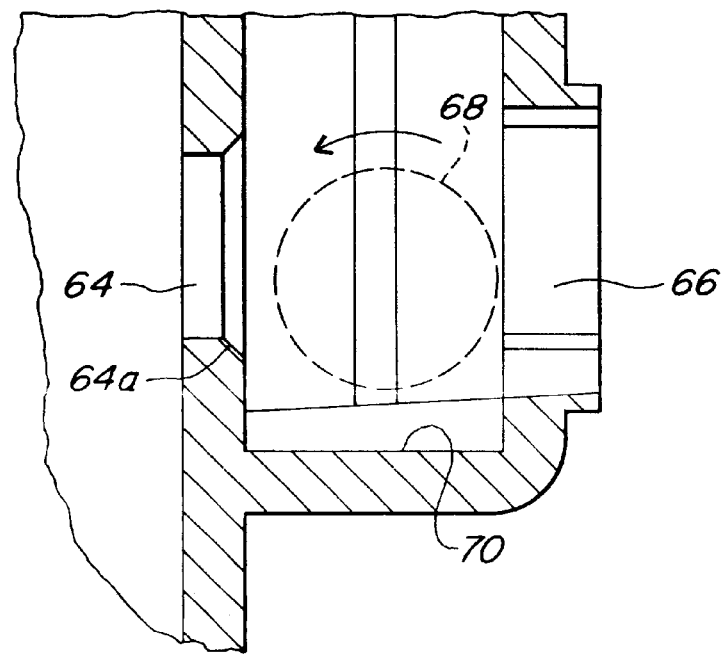
FIG. 9B is a cross-sectional view of the positive pressure protection valve of FIG. 9A in an open position, illustrating an opening to the outside environment, a tapered opening for access to the collection chamber of the fluid-recovery system, and a sealing ball for sealing the tapered opening.
Figure 10:
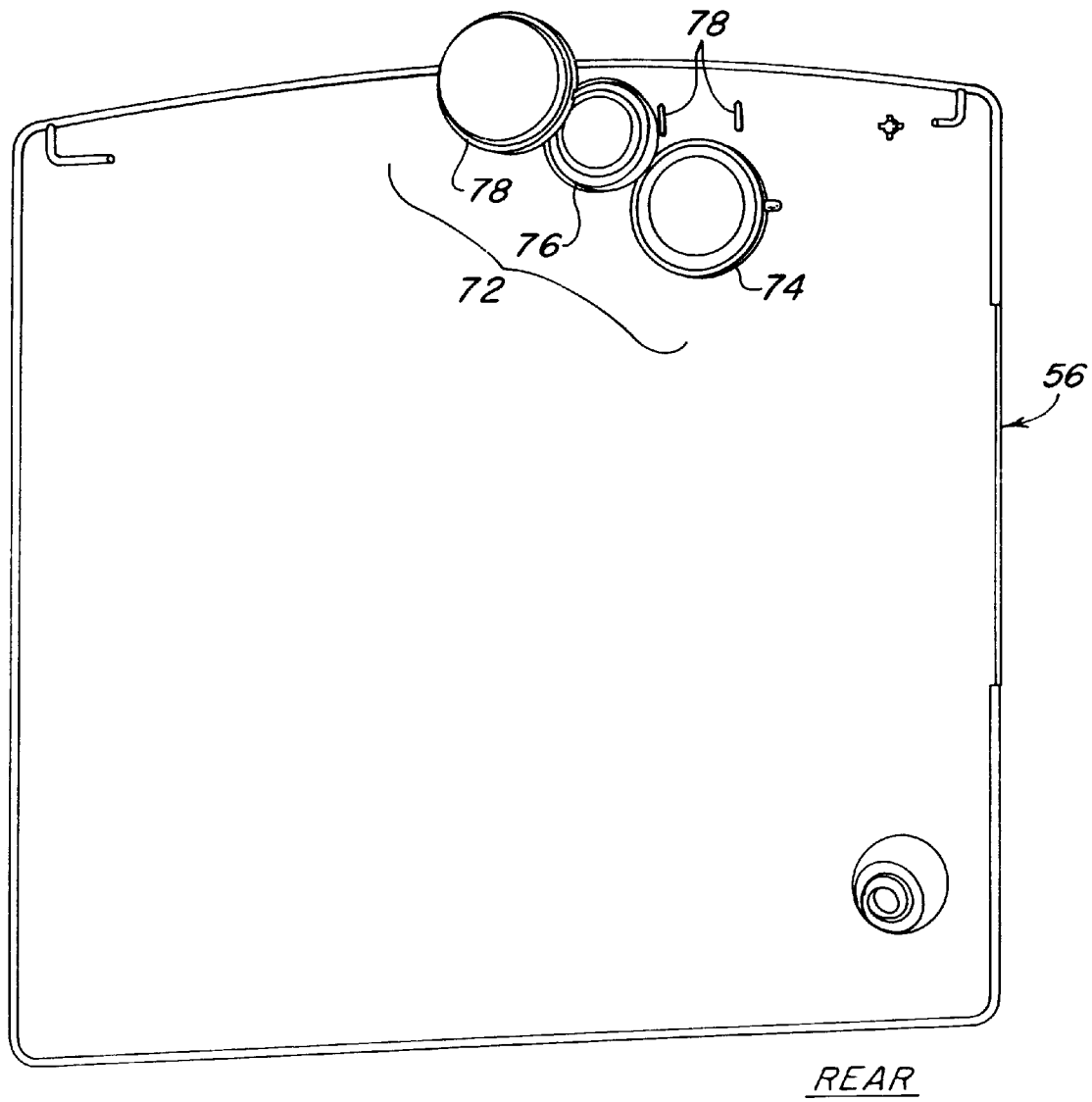
FIG. 10 is a perspective view of a front cover for the fluid-recovery system of FIG. 1, illustrating the components of a vacuum indicator including a seat integrally molded within the front cover, a diaphragm, and a cap in an exploded view.

With reference to FIGS. 1, 9A, and 9B, another feature of the illustrative fluid recovery system 10 is an integrally molded positive pressure relief valve 60 (herein "the PPRV") that extends above a top surface 12a of the housing 12. The PPRV 60 includes two side walls 60a, 60b, a rear wall 60c, and a top surface 60d that are arranged to provide a generally rectilinear cross-section for an integrally molded enclosure 62, although other shapes may also be utilized. The integrally molded enclosure 62 includes a base 62a having an opening 64 therein for providing air flow communication with the collection chamber 14 through the enclosure 20, and an opening 66 that is open to the outside environment. The opening 64 includes a tapered section 64a for seating a sealing ball 68, to provide an air-tight seal between the enclosure 20 and the outside environment.

In normal operation, the sealing ball 68 is seated within the tapered portion 64a of the opening 64, thereby closing the valve 60 and sealing the enclosure 20 from the outside environment. In the event that pressure within the collection chamber 14, and consequently within the enclosure 20, rises above an undesired level, e.g., above atmospheric pressure, the force from the air pressure unseats the sealing ball 68, thereby releasing air to the outside environment and restoring the pressure within the collection chamber to a safe level.

An undesirably high pressure within the enclosure 20 can develop, for example, in the event that a suction line attached to the fluid-recovery system 10 is occluded, or is shut off. In such a situation, the PPRV opens to relieve the pressure, thus protecting the patient from a pressure build-up within the fluid-recovery system 10.

With continuing reference to FIGS. 9A and 9B, the rear wall 60c of the illustrative integrally molded enclosure 62 includes a ramped rib 70 having an increased thickness proximate the top of the enclosure 62 and a decreasing thickness toward the base 62a, thus providing a surface sloped toward the opening 64. The ramped rib 70 is preferably formed during the manufacturing of the housing 12, for example through an injection molding process, as an integrally molded structure of the enclosure 62. Those skilled in the art will understand that any of the other surfaces 66a and 66b of the PPRV 60, or all of the surfaces 60a, 60b, and 60c, or any combination thereof can include a ramped rib. The ramped rib 70 operates to bias the sealing ball 68 toward the opening 64, when the fluid recovery system is destabilized from a normal operating orientation, i.e., an upright orientation.

For example, as shown in FIG. 9B, in the event that the fluid recovery system 10 is knocked over onto its rear surface, i.e., such that the rear wall of the housing 12 is parallel to the work surface upon which the fluid recovery system is positioned, and the sealing ball 68 is dislodged from the opening 64, the ramped rib 70 provides a rolling surface for the sealing ball 68 that facilitates return of the ball 68 to the tapered section 64a of the opening 64, thereby closing the valve. Before the return of the sealing ball to the opening 64, the enclosure 20 is exposed to atmospheric pressure as a result of air flow through the opening 64. The atmospheric pressure within the enclosure 20 causes the vacuum protection valve 22 to close, in a manner described above in connection with the operation of the vacuum protection valve 22, thereby protecting the vacuum in the collection chamber 14 until the sealing ball 68 returns to the opening 64.

A fluid-recovery system is typically pressure tested after manufacturing to ensure that there are no leaks in the system. In order to pressure test the system, various ports providing air flow between the system and the outside environment need to be properly sealed. To this end, the illustrative PPRV 60 further includes a raised structure 60d, preferably integrally molded to the housing 12, surrounding the opening 66, which provides a seat for a sealing element (not shown) for conveniently sealing the PPRV 60 from the outside environment when pressure testing the fluid-recovery system 10.

It is desirable to have a readily visible vacuum indicator on a fluid recovery system, such as the illustrative fluid-recovery system 10 of FIG. 1, for indicating negative pressure condition within the collection chamber 14. Such a vacuum indicator can indicate to a medical professional that a negative pressure exists in the pleural space of a patient attached to the fluid recovery system 10. FIGS. 10, 10A, 11A, and 11B show an illustrative vacuum indicator 72 according to the present invention that includes a valve seat 74, integrally molded in the front cover 56 of the fluid-recovery system 10, a translucent diaphragm 76, formed from an elastomeric material such as silicone, and a cap 78 for positioning the diaphragm 76 in the seat 74. The valve seat 74 includes integrally molded vents 80 for providing air flow between one side of the diaphragm 76, i.e., the side not facing the cap, and the outside environment.

To assemble the vacuum indicator 72, the diaphragm 76 is seated over the seat 74, and the cap 78 is secured to the valve seat 74 to compress the edges of the diaphragm 76 into sealing engagement with the seat 74.

Figure 11A:
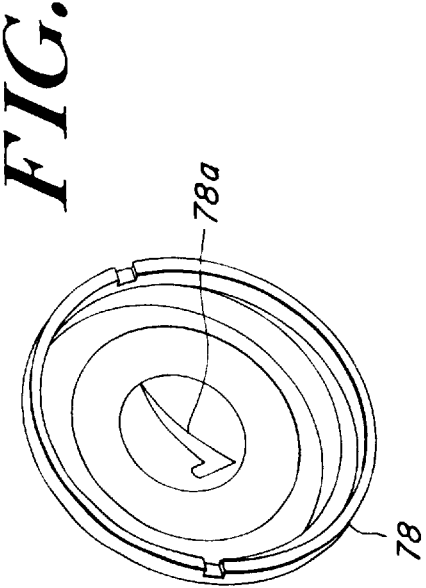
FIG. 11A is a front-elevational view of the inner surface of the cap of the vacuum indicator of FIG. 10, illustrating a marking on the inner surface of the cap.
Figure 11B:
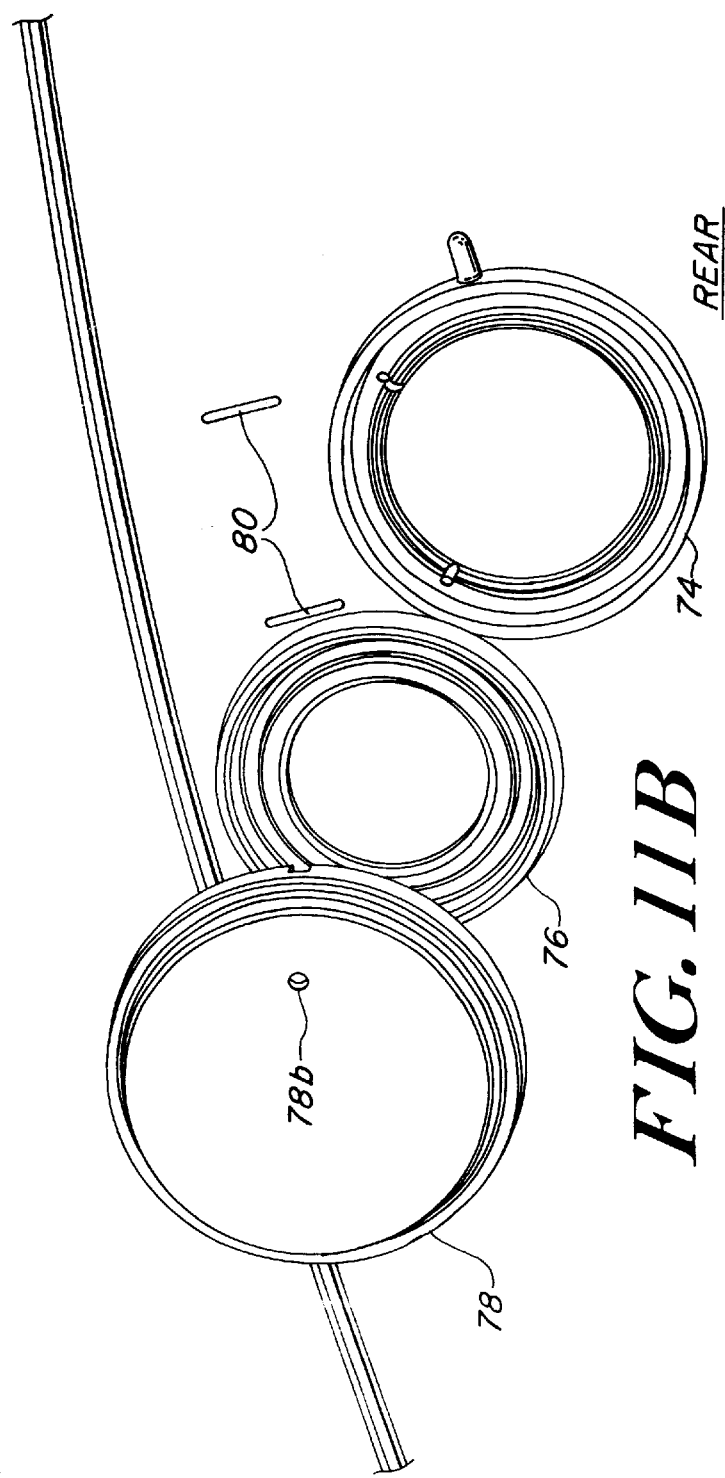
FIG. 11B is a perspective fragmentary view of the front cover of FIG. 10, further illustrating the seat, the diaphragm, and the cap of the vacuum indicator of FIG. 10 in an exploded view, and further illustrating vents integrally molded in the front cover for allowing air flow communication between one surface of the diaphragm and the outside environment and an opening the cap for air flow communication with the collection chamber of the fluid recovery system.

FIGS. 11A and 11B show that the cap 78 includes a marking 78a in the form of a "check mark" on its inner surface, i.e., the surface facing the diaphragm 76. Further, the cap 78 includes a port 78b therein that permits air from the interior of the housing 12 (FIG. 1) to communicate with the diaphragm 76.

FIGS. 12A and 12B illustrate the operation of the vacuum indicator 72. One side of the diaphragm 76 is in air flow communication with the outside environment through the vents 80, and the other side of the diaphragm 76 is at a pressure equal to the pressure within the cap 78. Thus, when pressure within the collection chamber 14 (FIG. 1), and consequently within the cap 78 that is in air flow communication with the collection chamber 14 through the port 78b (FIG. 11B), is substantially one atmosphere, there is no significant pressure differential across the diaphragm 76. The diaphragm 76 is hence in a relaxed position, as shown in FIG. 12A.

In the event of negative pressure in the collection chamber 14 or negative pressure in the pleural space of the patient, for example through application of suction to the fluid recovery system 10, a pressure differential across the diaphragm 76 develops. If the negative pressure in the collection chamber 14 is below a selected threshold, for example −1 centimeter of water, this pressure differential forces the diaphragm 76 to move in the direction of the inside surface of the cap 78, as shown by an arrow 80a, and to contact the inside surface of the cap 78, as shown in FIG. 12B. Upon contact of the translucent diaphragm 76 with the inside surface of the cap 78, the marking 78a becomes discernable through the translucent diaphragm 76 from outside of the fluid recovery system, thereby providing a visual indication of a negative pressure condition in the collection chamber.

An alternative embodiment of the fluid-recovery system of the invention includes a vacuum indicator that has the same components as those described above in connection with the vacuum indicator 72, but is manufactured as a separate component rather than an integral component of the housing 12. Such an alternative embodiment further includes a cover for its front face that is at least partially transparent. The separate vacuum indicator is placed within the housing such that it can be readily viewed through the transparent portion of the front cover, thereby providing an indication of a negative pressure condition in the collection chamber or in the pleural space of the patient.

Figure 13:
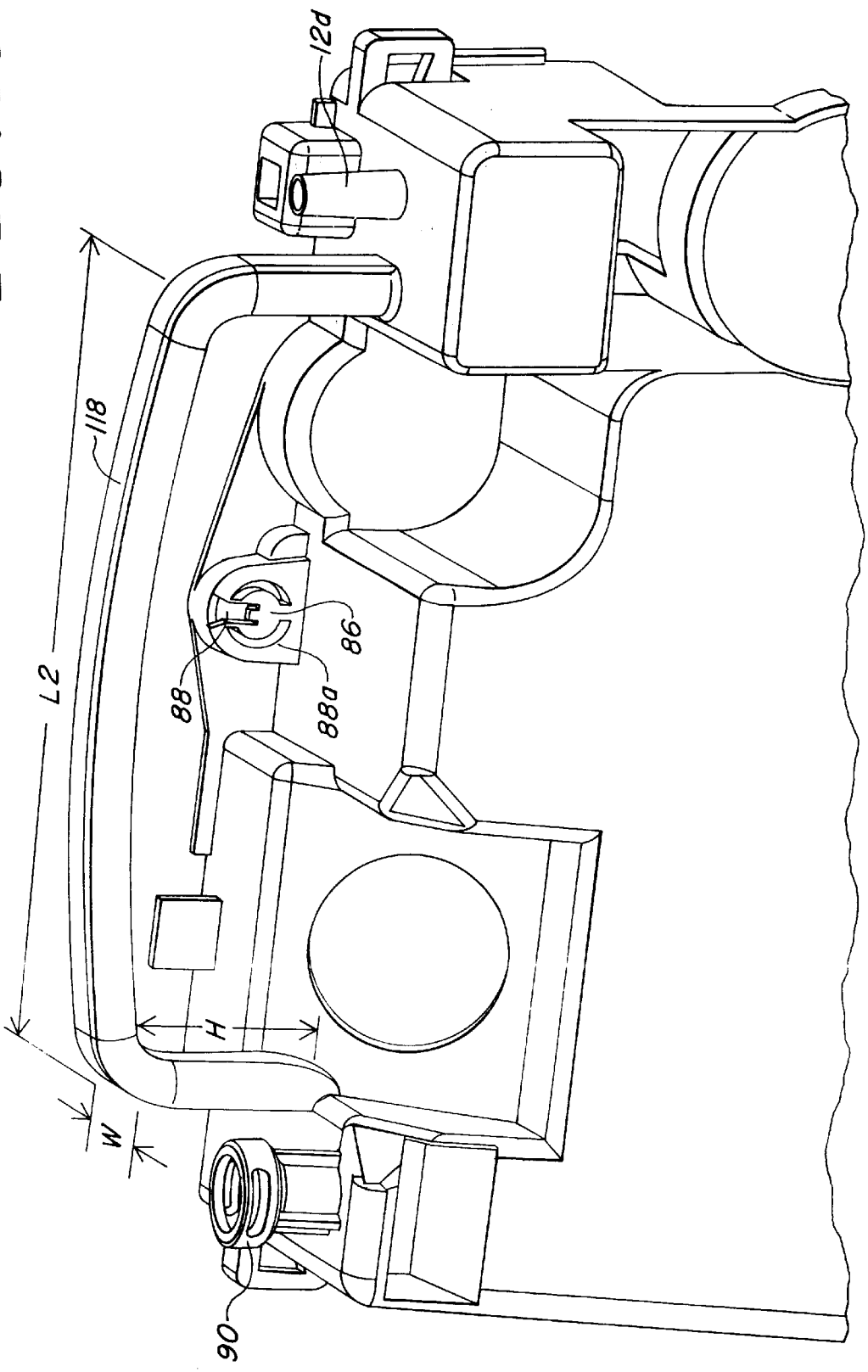
FIG. 13 is a perspective view of the top surface of the fluid-recovery system of FIG. 1 from the rear, illustrating an integrally molded connecting element for connecting the fluid-recovery system to a patient, and manually actuable pressure relief valve, and a handle sized and shaped for safe and easy transportation of the fluid-recovery system.

With reference to FIGS. 1 and 13, another aspect of the illustrative fluid-recovery system 10 relates to providing a manually actuable relief valve 82 for quickly relieving excess pressure in the collection chamber 14. The relief valve 82 extends above the top surface 12a of the housing 12 and includes an enclosure 84 that is integrally formed within the housing 12, and is in air flow communication with the collection chamber 14. The relief valve 82 further includes a diaphragm 86 sealing the enclosure 84 from the outside environment, and an integrally molded actuating element 88 that can, for example, be a hinged tab integrally molded to the housing 12.

In the event that the pressure in the collection chamber 14 rises above atmospheric pressure, the relief valve 82 can be manually activated by the actuating element 88 to release air from the collection chamber 14, thereby relieving the pressure in the chamber 14. In particular, manually depressing the actuating element 88 moves the diaphragm 86 to open the valve 82, thus releasing air from the collection chamber to the outside environment. Thus, the manually actuable relief valve 82 provides a mechanism for quickly relieving pressure in the collection chamber 14.

Figure 13A:
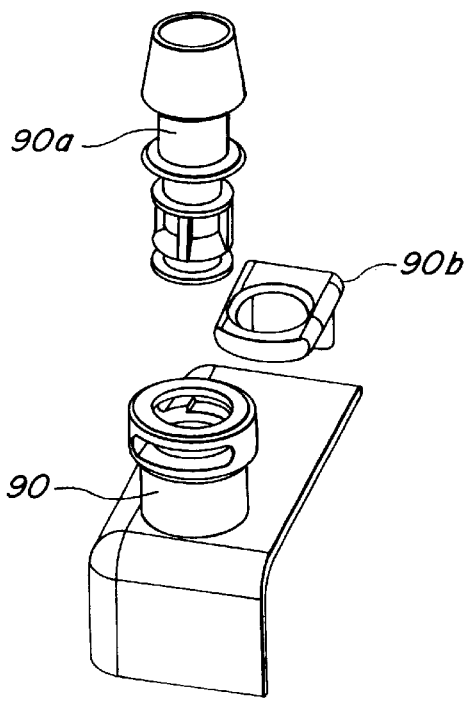
FIG. 13A is a perspective view of two mating portions and a positioning portion of a latching connector, where one of the mating portions is the connecting element of FIG. 13.
Figure 13B:
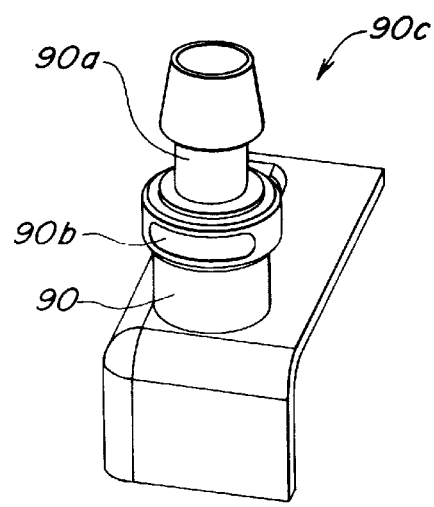
FIG. 13B is a perspective view of a latching connector obtained after assembly of the mating portions and the positioning portion shown in FIG. 13A.

In a hospital setting, it is important to be able to hook up a patient to a fluid-recovery system quickly and easily. To this end, the illustrative fluid-recovery system 12 includes a connecting element 90, shown in FIG. 13, that is integrally molded to the housing 12. As shown in FIGS. 13A and 13B, the illustrative connecting element 90, which is a portion of a latching connector, is configured to receive a mating connecting element 90a and a positioning element 90b to a form a latching connector 90c for receiving a flexible tube (not shown), to connect the patient to the recovery system. The connecting element 90 extends above the top surface 12a of the housing 12 so that it can be conveniently accessed by a medical professional. The integrally molded connecting element 90 can be preferably a male or a female portion of a latching connector.

One advantage of the integrally molded connecting element 90 is that it significantly simplifies connecting a patient to the fluid recovery system 10. The connection of a conventional fluid-recovery system to a patient typically requires holding a first flexible tubing attached to an input port of the recovery system with one hand, and using the other hand to connect an end of a second flexible tubing, whose other end is attached to the patient, to the first tubing. In contrast, a medical professional utilizing a fluid recovery system of the invention needs to use only one hand to connect a patient to the recovery system. For example, such a medical professional can simply engage a male portion of a latching connector attached to one end of a flexible tube, whose other end is attached to the patient, with the illustrative female portion of a latching connector 90, to connect the flexible tube to the fluid-recovery system 10. The flexible tube provides a passageway through the connecting element 90 for flow of fluid from the patient into the collection chamber 14.

Figure 14:
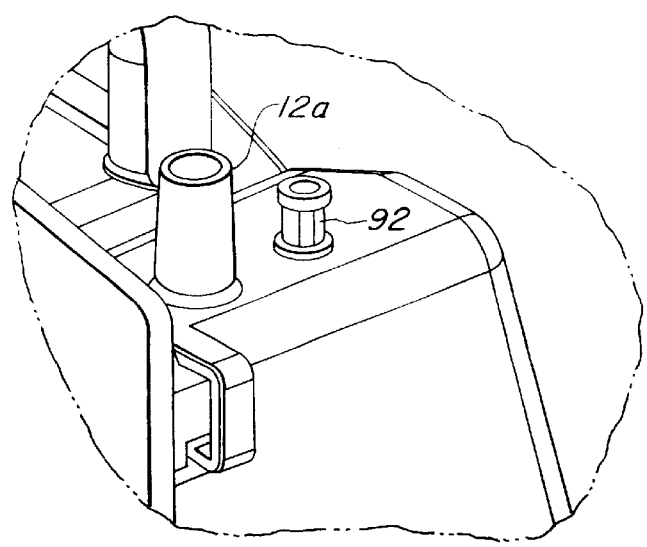
FIG. 14 is a fragmentary perspective view of the top surface of the fluid-recovery system of FIG. 1, illustrating the integrally molded connecting element of FIG. 13, and an integrally molded port for measuring pressure within the collection chamber of the fluid-recovery system.

With reference to FIG. 14, another feature of the illustrative fluid-recovery system 10 is an integrally molded port 92 that is configured to provide access to the collection chamber 14. In particular, the integrally molded port 92 can be employed to measure pressure in the collection chamber 14. For example, a pressure gauge (not shown) can be inserted into the collection chamber 14 through the integrally molded port 92, to measure pressure within the collection chamber 14.

Figure 15A:
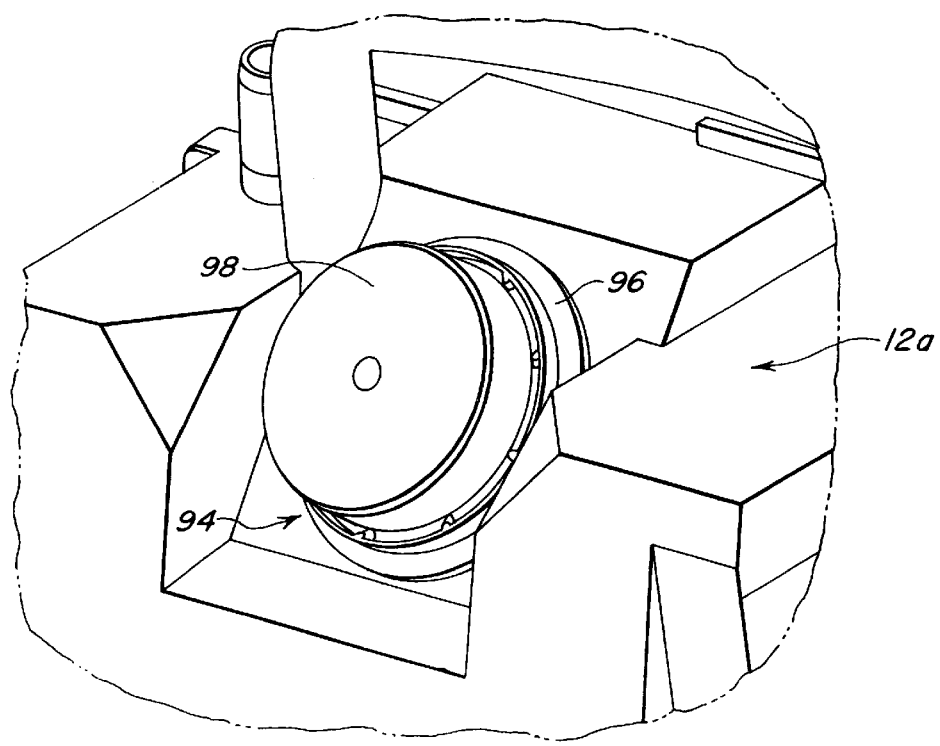
FIG. 15A is a fragmentary perspective view of the top surface of the fluid-recovery system of FIG. 1, illustrating a tamper-resistant disposal system for draining fluid collected within the fluid-recovery system or adding sterilizing agents to the collected fluid.
Figure 15B:
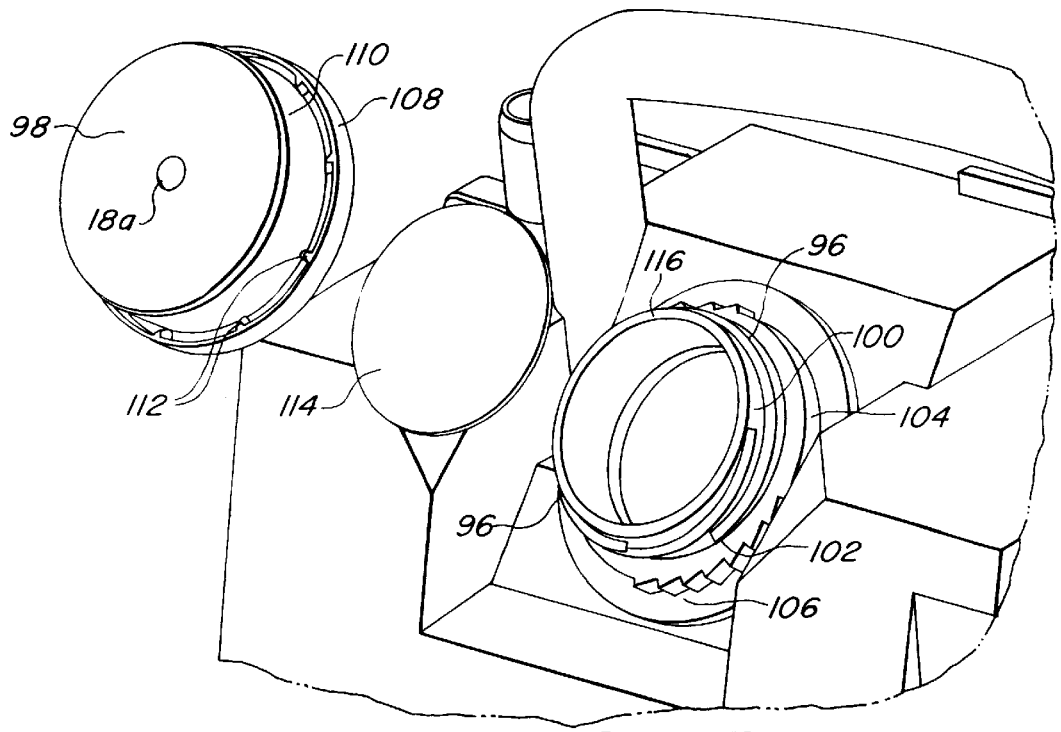
FIG. 15B is a perspective view of the tamper-resistant disposal system of FIG. 15A that includes an integrally molded disposal port, a seal, and a cap.

With reference to FIGS. 1, 15A and 15B, the illustrative fluid-recovery system 10 further includes a tamper-resistant disposal system 94 that allows proper disposal of fluid drawn from a patient and collected within the collection chamber 14. The disposal system 94 includes a disposal port 96 that is preferably positioned on the upper surface 12a of the housing 12, to provide access to each chamber within the housing 12. The disposal port 96 is preferably formed as an integral component of the housing 12. Alternatively, the disposal port 96 can be manufactured separately and be added to the housing 12 during or after the manufacture of the housing 12. A cap 98 closes the disposal port 96 during normal operation of the fluid-recovery 10, e.g., during collection of fluid from the patient.

The illustrative cap 98 is threadedly connected to the disposal port 98. In particular, a neck 100 of the disposal port 96 includes a number of threads 102 for coupling the cap 98, which includes a number of mating internal threads (not shown), to the disposal port 96. Alternatively, the cap 98 can be configured to fit on the disposal port 102 in a substantially friction-tight fit. Suitable alternative fastening mechanisms, including bonding by adhesive, can also be employed.

Further, a base 104 of the disposal port 96 includes a series of inclined ratchet-like teeth 106 extending the periphery thereof. A base 108 of the cap 98 includes a number of inclined, ratchet-like teeth (not shown) complementary in shape to the teeth 106 provided on the base 104 of the disposal port 96. The base 108 of the cap 98 is coupled to a body 110 of the cap 98 by a plurality of break-away tabs 112 spaced along the circumference of the cap body 110.

Fluid-recovery systems are generally delivered to medical personnel in a sterile condition prior to use, i.e., prior to connection to the patient. It is important that this sterile condition is maintained to prevent the spread of disease or infection to the patient. The illustrative disposal system 94 provides provisions for indicating whether the sterile condition of the fluid-recovery system 10 has been compromised, as discussed below.

When the cap 98 is positioned on the disposal port 96, the ratchet-like teeth of the cap 98 engage the ratchet-like teeth 106 of the disposal port 96, thus inhibiting motion of the cap base 108 relative to the base 104 of the disposal port 98. In the event that the cap 98 is rotated relative to the neck 100 of the disposal port 98, the cap base 108 is prohibited from rotating relative to the base 104 of the disposal port 98 by the ratchet-like teeth 106. As a result, the break-away tabs 112 shear and break, thus separating the base 108 of the cap 98 from the body 110 of the cap 98. Thus, the separated body 110 of the cap 98 provides evidence of tampering with the disposal system 94, or removal of the collected fluid from the fluid recovery system.

The disposal system 94 can further include a seal 114 positioned on a lip 116 of the neck 100 of the disposal port 96. The seal 114 is secured to the disposal port 96, preferably by an adhesive or the like, to inhibit air leakage through the disposal port 96. Before securing the seal 114 to the disposal port 96, a foil (not shown) is typically placed on the disposal port 96, and subsequently the seal 114 is secured to the disposal port 96 over the foil. The seal 114 is preferably complementary in shape to the lip 116 of the disposal port 96 and is preferably constructed from a material that is substantially impermeable to air, such as a metal or silicon foil. Removal of the seal 114 provides further indication of tampering with the disposal system 96, or removal of the collected fluid from the fluid recovery system. The cap 98 can optionally include a translucent portion 98a that allows visual inspection of the seal 114 without removing the cap 98.

In a hospital setting, fluid-recovery systems are frequently carried from one location to another, and further such systems may be handed from one medical professional to another. At times, such handling of the fluid-recovery system may result in an accidental fall of the system on the floor, which can result in breakage of the system and spillage of the fluid contained within the system. The spilled fluid may be contaminated, thus posing hazards to the medical personnel and the patients. Thus, it is important to provide provisions for safe handling of the fluid-recovery system, for example transportation of the system from one location to another.

Referring back to FIG. 13, the illustrative fluid-recovery system 10 of the invention can be easily and safely carried, and further it can be easily and safely transferred from one person to another. In particular, the illustrative fluid recovery system 10 includes a handle 118 that is preferably integrally formed in the top surface 12a of the housing 12 of the fluid-recovery system 10. The illustrative handle 118 is designed to have a length L2 of approximately 5 inches, and a width W of approximately 1 inch. The length of the handle 118 is selected to enable two medical professionals to simultaneously hold the handle 118, each with one hand. This allows a medical professional to transfer the fluid-recovery system 10 to another without any need to first place the fluid-recovery system 10 on the floor so that a second medical professional can grab it via the handle 118.

The illustrative handle 118 further has a height H, selected to be approximately 2 inches, to ensure that the handle 118 rises above other components, such as the connector 90 and the vacuum port 12d located on the top surface 12a of the housing 12. The raised height of the handle 118 provides some protection for the other components on the top surface 12a against accidental fall of objects on the fluid-recovery system 10. In particular, if an object accidentally falls on the fluid recovery system 10, it is likely that it would first hit the raised handle 118 rather than the other components on the top surface 12a. The impact of the object with the handle would divert the object away from the fluid-recovery system, thus minimizing any damage to the fluid-recovery system.

The illustrative handle 118 is preferably approximately centered in a front-to-back position and also laterally relative to the housing 12. This assures that the fluid-recovery system 10 is well balanced when fluid has been collected, and that the collection chamber 14 will not tilt excessively downward when the device is lifted.

Those skilled in the art will understand that the use of various components and structures described above is not limited to the above illustrative fluid-recovery system. In particular, the various components and structures described above can be utilized in fluid-recovery systems having both dry or wet suction regulator mechanisms.

It will thus be seen that the invention efficiently attains the objects set forth above, among those made apparent from the preceding description. Since certain changes may be made in the above constructions without departing from the scope of the invention, it is intended that all matter contained in the above description or shown in the accompanying drawings be interpreted as illustrative and not in a limiting sense. For example, although some integrally molded enclosures in the above illustrative embodiment are cylindrical, it is clear to those skilled in the art that other shapes can also be utilized for these enclosures.

What is claimed is:

1. A fluid recovery system for collecting fluid from a patient comprising
    a housing having a collection chamber for collecting the fluid,
    a valve for controlling fluid flow within the fluid recovery system, the valve including an upper detachable valve member that selectively engages a lower valve seat surrounding a fluid opening to seal the fluid opening, the lower valve seat being integrally molded to the housing of the fluid recovery system.

2. The fluid recovery system of claim 1, wherein the valve is a vacuum protection valve providing air flow communication with the collection chamber to permit air flow in one direction out of the chamber.

3. The fluid recovery system of claim 2, wherein the valve member is constructed of an elastomeric material and has a generally umbrella-like shape.

4. The fluid recovery system of claim 1, wherein the fluid recovery system is a chest drain.

5. The fluid recovery system of claim 1, wherein the valve is a negative pressure protection valve that opens to provide air flow between the collection chamber and the outside environment through the fluid opening when pressure in the collection chamber is lower than a predefined threshold.

6. The fluid recovery system of claim 5, wherein the negative protection valve further includes a valve housing for seating a spring and the valve member, said valve member being biased by the spring against said integrally molded valve seat to seal the fluid opening, wherein a pressure in the collection chamber lower than the predefined threshold causes the spring to contract thereby moving the valve member and providing air flow between the collection chamber and the outside environment.

7. The fluid recovery system of claim 6, wherein said valve housing is integrally molded to said housing of said fluid recovery system.

8. The fluid recovery system of claim 6, further comprising an integrally molded raised structure protruding outwardly from the fluid opening and configured to inhibit occlusion of the opening.

9. The fluid recovery system of claim 8, wherein said raised structure includes a hollow frusta-conical member surrounding the opening from the outside and having ports for providing air flow from the outside environment through the opening.

10. The fluid recovery system of claim 6, wherein the valve housing includes a first cylindrically tubular portion for receiving the spring and extending to a second portion for seating the valve member, the second portion of the valve housing having at least gone port therein for providing air flow between the valve housing and the collection chamber.

11. A fluid recovery system for collecting fluid from a patient, comprising
    a housing having a collection chamber for collecting a volume of the fluid from the patient, and
    a vacuum protection valve for allowing air flow in one direction out of the collection chamber, said vacuum protection valve including an enclosure integrally molded within the housing that has a base extending to an opening for providing air flow communication with the collection chamber.

12. The fluid recovery system of claim 11, wherein the vacuum protection valve includes a hollow flexible retaining member, the valve being secured to the housing by snap action placement of the flexible retaining member in said opening.

13. The fluid recovery system of claim 12, wherein the vacuum protection valve includes an umbrella valve member for sealing the opening, thereby providing one way air flow through the opening.

14. The fluid recovery system of claim 13, wherein the vacuum protection valve further includes a retaining member for retaining the umbrella valve member over the opening.

15. A fluid recovery system for collecting fluid from a patient, comprising
    a housing having a collection chamber for collecting a volume of the fluid from the patient, and
    a positive pressure relief valve for reducing pressure in the collection chamber when the pressure in the chamber exceeds a pre-defined value,
    wherein said positive pressure relief valve includes an integrally molded enclosure formed in said housing, said integrally molded enclosure having an integrally molded ramped rib.

16. The fluid recovery system of claim 15, wherein said integrally molded enclosure includes a first opening for air flow communication with the collection chamber and a second opening for air flow communication with the outside environment, said first opening being sealed by a sealing ball to provide a fluid-tight seal between the collection chamber and the integrally molded enclosure, said ball being dislodged from the first opening when pressure within the collection chamber exceeds the pre-defined value to allow air flow between the collection chamber and the outside environment, and wherein said integrally molded ramped rib provides a rolling surface to bias the ball toward said first opening when said fluid recovery system is destabilized from a normal operating orientation.

17. The fluid recovery system of claim 16, wherein the positive pressure relief valve further includes an integrally molded raised surface surrounding the second opening, said raised surface providing a valve seat for a sealing element to seal the housing from the outside environment.

18. A fluid-recovery system for collecting fluid from a patient, comprising
   a housing having a front face and a collection chamber for collecting a volume of fluid from the patient, and
   a vacuum indicator for indicating when pressure in the collection chamber is below a selected threshold, the vacuum indicator including
      an integrally molded seat in the front face of the housing,
      a translucent diaphragm positioned in the seat, and
      a cap mounted to the seat to compress the diaphragm into sealing engagement with the seat, the cap having a marking on a surface facing the diaphragm and further having an opening that provides air flow between the collection chamber and the diaphragm.

19. The fluid-recovery system of claim 18, wherein the diaphragm is formed of an elastomeric material.

20. The fluid recovery system of claim 18, wherein the front face includes a translucent portion and the vacuum indicator is positioned within the housing such that it is externally visible through the translucent portion of the front face, and the diaphragm contacts the marked surface of the cap when pressure within the collection chamber is below the selected threshold, thereby rendering the marker visible.

21. A fluid-recovery system for collecting fluid from a patient, comprising
   a housing having a front face, said front face having a translucent portion and said housing further having a collection chamber for collecting a volume of the fluid from the patient, and
   a vacuum indicator for indicating when pressure in the collection chamber is below a selected threshold, the vacuum indicator including
      a seat,
      a translucent diaphragm positioned in the seat, and
      a cap mounted to the seat to compress the diaphragm into sealing engagement with the seat, the cap having a marking on a surface facing the diaphragm and further having a n opening that provides air flow between the collection chamber and the diaphragm,
   wherein the vacuum indicator is positioned within the housing such that it is externally visible through the translucent portion of the front face, and the diaphragm contacts the marked surface of the cap when pressure within the collection chamber is below the selected threshold, thereby rendering the marker visible.

22. A fluid-recovery system for collecting fluid from a patient, comprising
   a housing having a top surface and a collection chamber for collecting a volume of the fluid from the patient, and
   a pressure relief valve having a manually actuable diaphragm sealing an integrally molded enclosure within the top surface from outside environment, the molded enclosure being in air flow communication with the collection chamber, and the diaphragm being manually actuated by an integrally molded actuating element to provide air flow between the collection chamber and the outside environment to reduce pressure in the collection chamber.

23. A fluid recovery system for collecting fluid from a patient, comprising
   a housing having a collection chamber for collecting the fluid, and
   a tamper-resistant disposal system for disposal of the collected fluid, wherein the tamper-resistant disposal system comprises:
      a disposal port integrally formed within said housing,
      a seal positioned on said disposal port for sealing said disposal port, and
      a cap having a cap body, a cap base, and a plurality of break-away tabs along a circumference thereof, said break-away tabs joining said cap body to said cap base, said cap being secured to said disposal port to close said disposal port.

24. The fluid-recovery system of claim 23, wherein said disposal port includes a first plurality of ratchet-like teeth and said cap includes a second plurality of ratchet-like teeth, said first and second plurality of ratchet-like teeth being in mating engagement upon threaded engagement of said cap with said disposal port to inhibit rotation of said base relative to said disposal port when said cap body is rotated relative to said disposal port.

25. The fluid-recovery system of claim 24, wherein said cap includes a translucent portion to allow visual inspection of said seal.

\* \* \* \* \*